(12) United States Patent
Casale et al.

(10) Patent No.: US 10,493,218 B2
(45) Date of Patent: Dec. 3, 2019

(54) DEVICE FOR DELIVERY OF AN AEROSOL SUBSTANCE

(71) Applicant: BIOMEDICAL RESEARCH IN OTOLARYNGOLOGY SRL B.R.I.O. S.R.L., Rome (IT)

(72) Inventors: Manuele Casale, Rome (IT); Roberto Lupo, Rome (IT); Fabrizio Salvinelli, Rome (IT)

(73) Assignee: BIOMEDICAL RESEARCH IN OTOLARYNGOLOGY SRL B.R.I.O. S.R.L. (IT)

( * ) Notice: Subject to any disclaimer, the term of this patent is extended or adjusted under 35 U.S.C. 154(b) by 690 days.

(21) Appl. No.: 15/028,414

(22) PCT Filed: Oct. 7, 2014

(86) PCT No.: PCT/IB2014/065121
§ 371 (c)(1),
(2) Date: Apr. 8, 2016

(87) PCT Pub. No.: WO2015/052653
PCT Pub. Date: Apr. 16, 2015

(65) Prior Publication Data
US 2016/0250423 A1 Sep. 1, 2016

(30) Foreign Application Priority Data

Oct. 11, 2013 (IT) .............................. RM2013A0562

(51) Int. Cl.
*A61M 11/00* (2006.01)
*A61M 15/08* (2006.01)
*A61M 15/00* (2006.01)

(52) U.S. Cl.
CPC ........ *A61M 11/007* (2014.02); *A61M 15/009* (2013.01); *A61M 15/08* (2013.01)

(58) Field of Classification Search
CPC .... A61M 1/00; A61M 1/0019; A61M 1/0021; A61M 3/00; A61M 3/02; A61M 3/0233;
(Continued)

(56) References Cited

U.S. PATENT DOCUMENTS 1,943,092 A * 1/1934 Seyforth ................. B05B 11/06
239/103
3,236,458 A * 2/1966 Ramis .................... A61M 11/00
128/200.18
(Continued)

FOREIGN PATENT DOCUMENTS

| CN | 1101004 A | 4/1995 |
|---|---|---|
| CN | 2724849 Y | 9/2005 |

(Continued)

OTHER PUBLICATIONS

International Search Report for International Application No. PCT/IB2014/065121 filed on Oct. 7, 2014 in the name of Manuele Casale et al., dated Jan. 19, 2015.
(Continued)

*Primary Examiner* — Timothy A Stanis
*Assistant Examiner* — Matthew D Ziegler
(74) *Attorney, Agent, or Firm* — Shuttleworth & Ingersoll, PLC; Timothy J. Klima

(57) ABSTRACT

A device for delivering a substance in the form of aerosol is described. The device is used with a syringe equipped with a plunger and without a needle. The delivery device comprises: a connection sleeve for connecting the device with the syringe; a nozzle for delivering the substance as aerosol, preferably with troncoconical walls and obtained on an elongated outer body of the device; and a fluid-dynamic path comprised between the connection sleeve and the dispensing nozzle, wherein the path comprises an annular expansion chamber and an elongated acceleration chamber, so that,
(Continued)

while in use, a manual actuation of the plunger introduces the substance into the fluid-dynamic path in a liquid form through the connection sleeve and produces the substance as aerosol through the dispensing nozzle.

11 Claims, 7 Drawing Sheets

(58) Field of Classification Search
CPC .............. A61M 3/0254; A61M 3/0262; A61M 3/0279; A61M 5/00; A61M 5/178; A61M 5/30; A61M 5/31; A61M 5/3129; A61M 5/3134; A61M 5/3135; A61M 5/315; A61M 11/00; A61M 11/001; A61M 11/007; A61M 15/009; A61M 15/08; A61M 2210/0618; A61M 2005/1787; A61M 2209/06; A61M 11/006–008; A61M 11/02; A61M 11/06; A61M 11/08; A61M 15/06; B05B 1/00; B05B 1/02; B05B 1/06; B05B 11/00; B05B 11/0035; B05B 11/0089; B05B 11/06; B05B 11/062; B05B 11/30; B05B 11/3001; B05B 11/3002; B05B 11/3004; B05B 11/3015; B05B 11/007; B05B 9/00; B05B 9/03; B05B 9/04; B05B 9/0413; B05B 9/043; B05B 9/047; B65D 83/14; B65D 83/28; B65D 83/30; B65D 83/303; A24F 47/002
USPC .................................. 239/338, 370, 589, 601
See application file for complete search history.

(56) References Cited

U.S. PATENT DOCUMENTS

| | | | | |
|---|---|---|---|---|
| 3,251,556 | A * | 5/1966 | Burnham | B05B 1/267 239/103 |
| 3,961,756 | A * | 6/1976 | Martini | B05B 1/12 239/337 |
| 4,235,235 | A * | 11/1980 | Bekkering | A61M 5/3129 604/238 |
| 4,344,573 | A * | 8/1982 | De Felice | B05B 11/02 128/203.15 |
| 4,511,087 | A * | 4/1985 | Matsumoto | B05B 7/0433 239/430 |
| 4,708,292 | A * | 11/1987 | Gammons | B29B 7/7678 239/414 |
| 4,830,284 | A * | 5/1989 | Maerte | B05B 11/0067 239/333 |
| 5,217,442 | A * | 6/1993 | Davis | A61M 5/14276 604/191 |
| 5,224,471 | A * | 7/1993 | Marelli | B05B 11/0005 128/200.14 |
| 5,370,318 | A * | 12/1994 | Weston | B05B 11/0064 222/494 |
| 5,505,193 | A * | 4/1996 | Ballini | A61H 35/04 128/200.14 |
| 5,520,337 | A * | 5/1996 | Fuchs | B05B 7/0031 239/343 |
| 6,158,676 | A * | 12/2000 | Hughes | A61M 11/06 239/337 |
| 6,334,552 | B1 * | 1/2002 | Bougamont | B05B 11/3001 222/341 |
| 8,393,555 | B2 * | 3/2013 | Niemela | D21G 7/00 239/399 |
| 9,067,034 | B2 | 6/2015 | Djupesland et al. | |
| 9,205,208 | B2 | 12/2015 | Djupesland | |
| 2002/0174864 | A1 * | 11/2002 | Alchas | A61M 15/08 128/200.14 |
| 2005/0205611 | A1 * | 9/2005 | Bonney | B05B 11/0048 222/282 |
| 2006/0162722 | A1 * | 7/2006 | Boehm | A61M 11/06 128/200.14 |
| 2010/0163045 | A1 | 7/2010 | Powell et al. | |

FOREIGN PATENT DOCUMENTS

| | | |
|---|---|---|
| CN | 101918061 A | 12/2010 |
| GB | 2 272 389 A | 5/1994 |
| GB | 2272389 B | 7/1996 |
| RU | 2319513 C2 | 3/2008 |
| WO | 2010/123347 A1 | 10/2010 |
| WO | 2011/015850 A1 | 2/2011 |

OTHER PUBLICATIONS

Written Opinion for International Application No. PCT/IB2014/065121 filed on Oct. 7, 2014 in the name of Manuele Casale et al., dated Jan. 19, 2015.

Chinese Office Action dated Aug. 23, 2018 and Search Report dated Aug. 13, 2018 from counterpart Chinese App No. CN105636629.

* cited by examiner

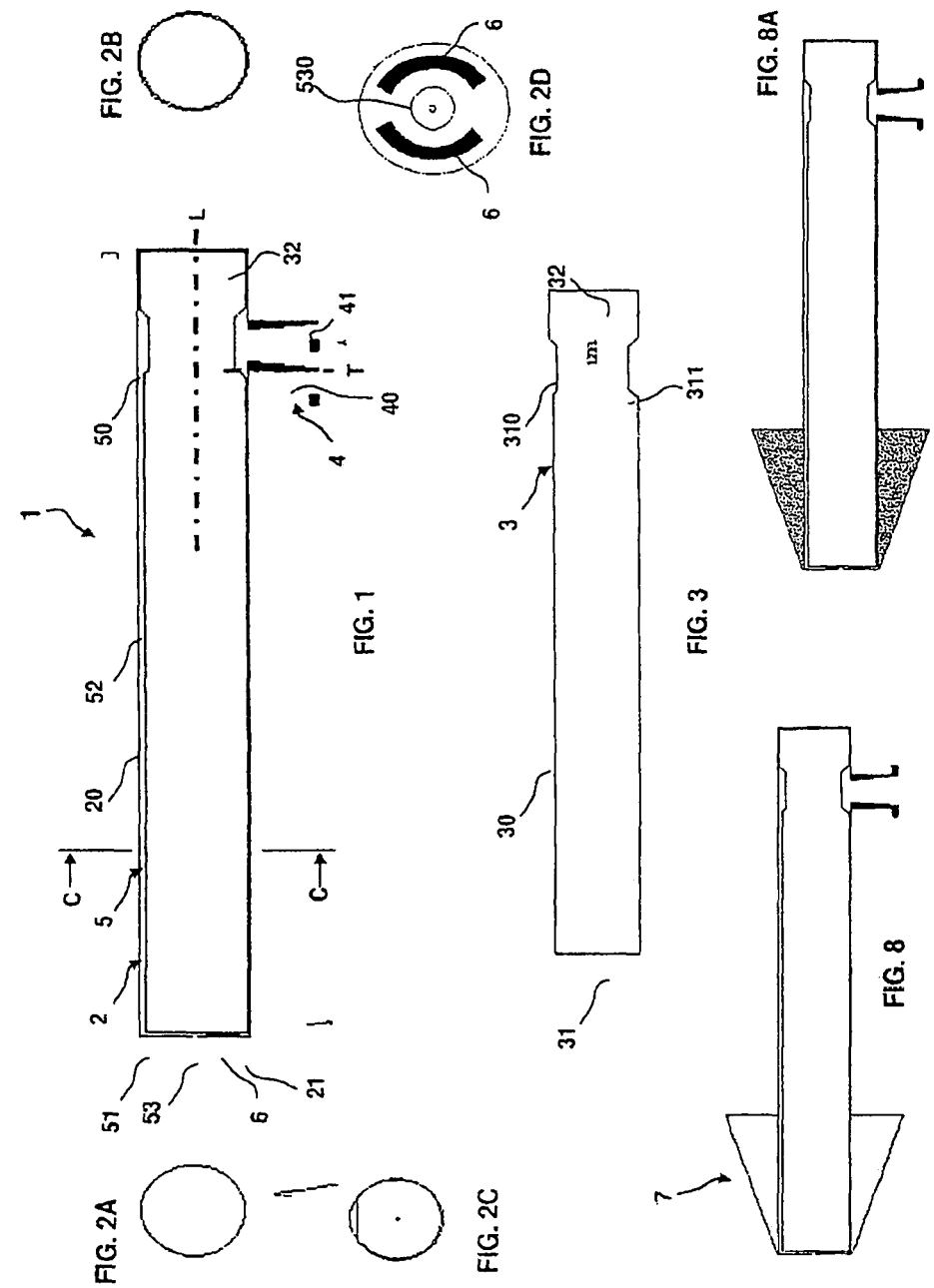

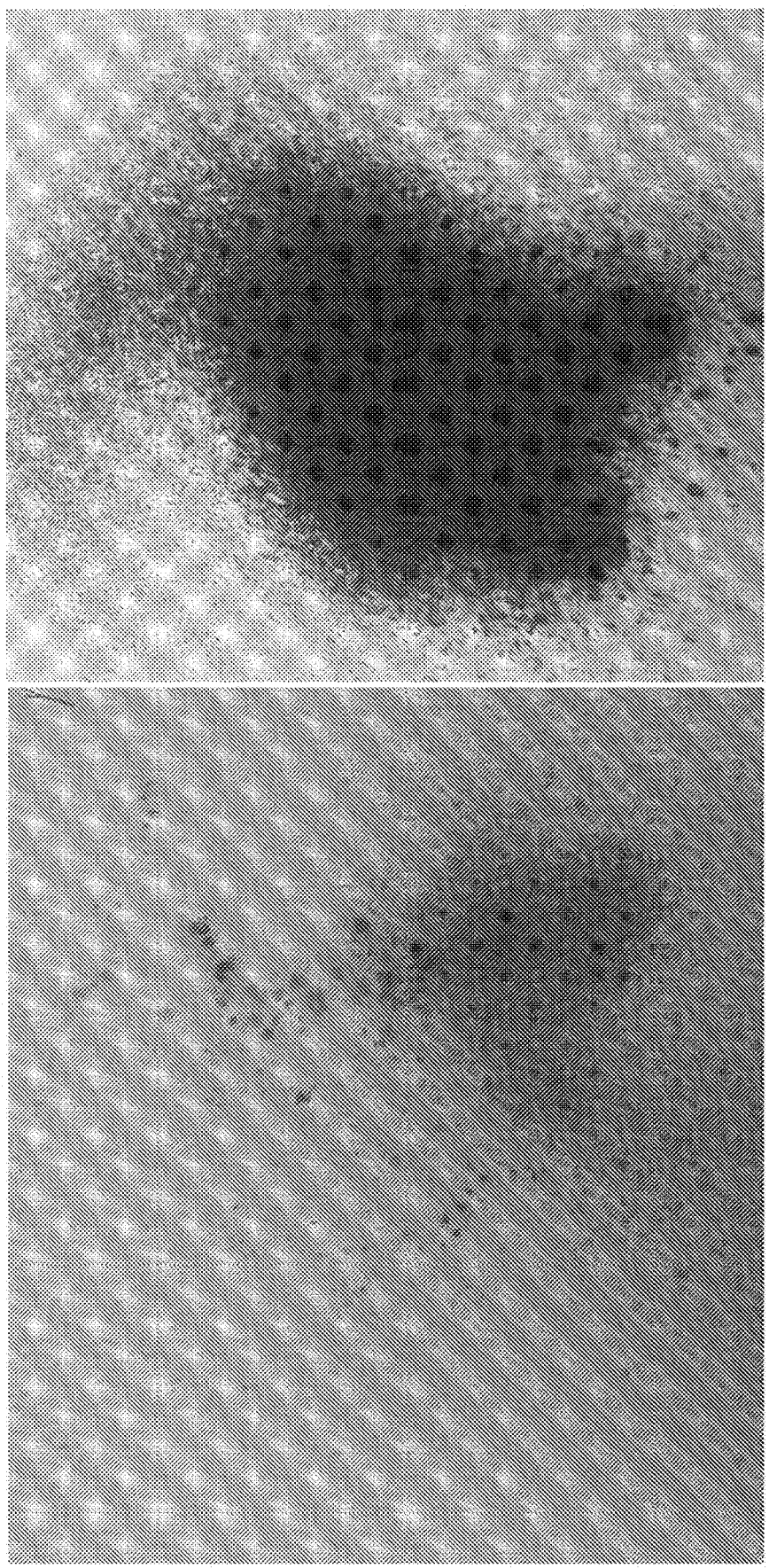

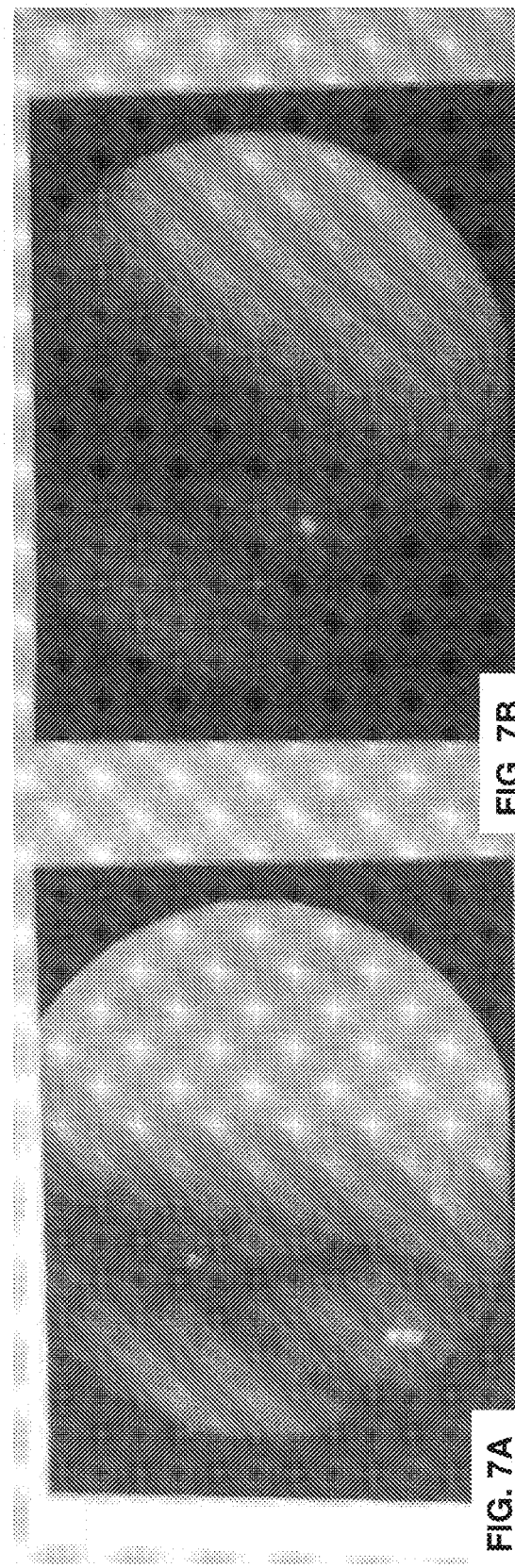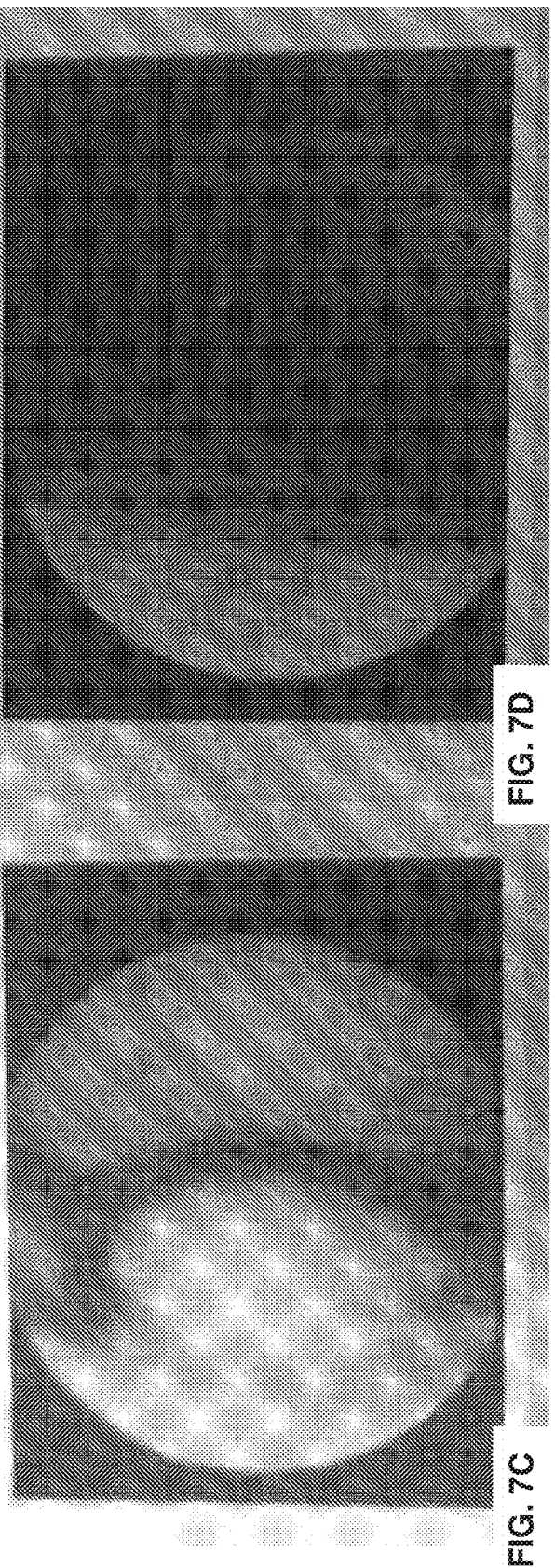
FIG. 7A  FIG. 7B  FIG. 7C  FIG. 7D

DEVICE FOR DELIVERY OF AN AEROSOL SUBSTANCE

CROSS REFERENCE TO RELATED APPLICATIONS

The present application is the U.S. national stage entry of International Patent Application No. PCT/IB2014/065121, filed internationally on Oct. 7, 2014, which, in turn, claims priority to Italian Patent Application No. RM2013A000562, filed on Oct. 11, 2013.

TECHNICAL FIELD OF THE INVENTION

The present invention relates to a delivery device of a substance in the form of aerosol and in particular to a device which can be actuated (even) manually.

BACKGROUND

In the last years the topic administration of drugs by nasal inhalant has been more and more spreading, above all for the treatment of acute and chronic inflammatory processes and for pharmaceutical substances which otherwise have to be administered by parental (invasive) route. The nasal inhalant has the following advantages with respect to the oral or parental route:

- the drug avoids the first passage effect and the gastro-intestinal metabolism,
- the drug is quickly absorbed thanks to the high permeability and vascularisation of the nasal mucosa,
- the administration route is not invasive and then minimizes the risk of infections,
- a specific training is not requested for the administration,
- trauma to the patient are not created.

The topic treatments for both acute and chronic rhynosinusal pathologies have become of common use by otorhinolaryngolists and primary care physicians, in particular for the treatment of sinusitis and specifically of rhynosinusitis.

The sinusitis treatment has the following main objectives:

- to re-establish the right drainages of the rhynosinual secretions,
- to check or remove the inflammation source,
- to ease the symptoms, above all pain and the sensation of nasal congestion.

In order to reach such objectives actually different therapeutic options are applied, in particular:

- cortico-steroidal anti-inflammatory drugs to reduce the inflammation and the mucosal edema,
- mucolytic agents to fluidify the secretions,
- antihistaminics to reduce secretions and the mucosal reactivity, especially in the allergic subject,
- nasal decongestants to reduce the nasal obstruction,
- anticholinergics to reduce secretions,
- antibiotics to fight the infections.

The intranasal administration of the above-mentioned drugs, with respect to the administration by oral route, can have the advantage of being a more rapid and not invasive route and of allowing to administer smaller doses with respect to the oral route, reaching directly the "target" site, with consequent smaller side effects.

The main targets of the nasal topic therapy are represented by:

- the osteo-meatal complex, the structure near the ostium of the maxillary sinus, the most important site for draining the maxillary, etmoid and front sinus; an obstruction at such level on anatomical or inflammatory basis often represents the "primum movens" of a sinusal inflammation,
- the (upper medium and above all the lower) nasal concha which, if inflamed, cause the drainage block of the sinuses and a reduction in the respiratory nasal space,
- the rear portion of the nasal fossa and the sphenoethmoidal recess, drainage site of the sphenoidal sinus,
- the paranasal sinuses themselves, by considering that in most cases the most involved sinuses in both acute and chronical inflammatory processes are represented by the maxillary sinus and by the etmoidal sinus.

Such nasal topical treatments provide the nebulization of the substance to be administered in the rhynosinusal cavities. The nebulization, according to the sizes of the nebulized particles, can be performed in the form of spray or aerosol. The sizes of the nebulized particles influence the administration time and above all the penetration depth and the distribution of the nebulized substance in the rhynosinusal cavities.

In particular, the spray allows nebulizing the particles with larger diameter, it inserts a small quantity of product in the nasal cavities and it reaches easily the most anterior portion of the same cavities, in particular the head of the inferior nasal concha, by distributing in the most rear portions of the nasal fossae in small quantity by means of the mucociliary clearance.

The aerosol nebulization allows obtaining smaller particles, it allows administering a greater quantity of substance in the nasal fossae and obtaining, indeed thanks to the more limited diameter of the particles, the medium meatus and the deeper portions of the nasal fossae, by allowing a better distribution of the drug.

The drawbacks of the current systems of spray nebulization are mainly represented by:

- reduced quantity of drug inserted in the nasal fossae,
- distribution of the drug mainly at the level of the head of the inferior nasal concha and in the third inferior one of the nasal fossa and only in small quantity in the remaining portion of the nasal fossa,
- rather high production and sale costs.

In principle, the nebulization by means of aerosol is preferable from a therapeutic point of view in the treatment of the rhynosinusal cavities, by virtue of the better penetration and distribution of the drug. However, even the current systems of aerosol nebulization have some important drawbacks, and in particular:

- long administration time,
- the difficulty/impossibility of nebulizing viscous substances,
- the need for often bulky devices, with need for outer energy source, typically an electric socket,
- the engagement of keeping high hygiene standards downstream of each administration,
- however rather high production and sale costs.

It is also to be noted that several of the devices for nebulizing drugs in the rhynosinusal cavities in fact are conceived for inflammatory pathologies of the lower respiratory tracts and "adapted" for the rhynosinusal cavities themselves.

SUMMARY OF THE INVENTION

The technical problem placed and solved by the present invention is then to provide a delivery device of a substance in the form or aerosol allowing to obviate the drawbacks mentioned above with reference to the known art.

Preferred features of the present invention are subject of the depending claims.

The device of the invention allows a topic administration in the rhynosinusal cavities, resulting comfortable like a spray and effective like an aerosol nebulization. The device can be easily used for all drugs which can be administered via the nose, including vaccines, insulin, analgesic drugs, for the treatment of cephalea and other potentially effective drugs if administered via the nose.

Preferably—and as it will be explained better hereinafter—the device is suitable to be used in combination with a common syringe which can be actuated manually and having different capabilities depending upon the quantity of drug to be administered. The syringe—and in particular the delivery end of this one (without needle)—is connected to the device of the invention, for example by means of simple pressure or screw snap-in thanks to a specific thread existing both on the syringe and on the device. In this way, the user actuates the plunger of the syringe to determine the passage of the liquid drug within the delivery device, and inside the latter the substance is nebulized and it outgoes for the direct administration in the nose in the form of an aerosol.

The device includes a fluidodynamic path based upon an expansion chamber and an acceleration chamber arranged in sequence and suitable to determine an optimum delivery of fluid, according to what illustrated hereinafter.

In particular, the device allows:
- the nebulization at aerosol level of substances even with high viscosity, thanks to the possibility of the manual actuation and the effective nebulization mechanism;
- very low administration time, in particular even in the order of seconds (of course even depending upon the quantity of drug which one wants to administer);
- the possibility of modulating easily the quantity of drug according to the needs and the drug itself;
- a larger distribution of the drug on the mucosae with respect than sprays;
- a very low manufacturing and sale cost;
- high hygiene standards, thanks to the possibility of manufacturing the device as disposable (single-use) device and to the fact that it can be provided as personal administrator;
- reduced sizes and portability, with use possibility everywhere without the need of outer energy sources and in particular of electrical energy;
- by virtue of what just illustrated, the possibility of reaching poor populations with otherwise inaccessible treatments;
- the possibility of making a series of drugs more usable and to revise the administration methodology.

Even by virtue of the above-illustrated features, the device of the invention can be defined a "spray-sol".

Other advantages, features and use modes of the present invention will result evident from the following detailed description of some embodiments, shown by way of example and not with limitative purpose.

BRIEF DESCRIPTION OF THE FIGURES

The figures of the enclosed drawings will be referred to, wherein:

FIG. 1 shows a view in longitudinal section of a preferred embodiment of the device according to the present invention;

FIGS. 2A and 2B show each one a front and rear view of the device of FIG. 1, respectively;

FIG. 2C shows a cross-section view of the device of FIG. 1, performed according to the line C-C of the latter figure;

FIG. 2D shows an enlarged detail of the view of FIG. 1, in particular a cross section performed at the level of a dispensing nozzle of the device;

FIG. 3 shows a side view of an inner body of the device of FIG. 1;

FIGS. 6A and 6B show the results of preliminary comparative delivery tests, respectively with a commercial spray and with the device of FIG. 1;

FIGS. 7A to 7D relate to images acquired with optical probe in the rhynosinusal cavities, respectively with a known spray at different depths (FIGS. 7A and 7C) and with the device of FIG. 1 at the same depths (FIGS. 7B and 7D);

FIGS. 8 and 8A show each one a view in longitudinal section of the device of FIG. 1, bearing an accessory for coupling with the nasal cavity, made of spongy material in case of FIG. 8A;

Figure 4B:
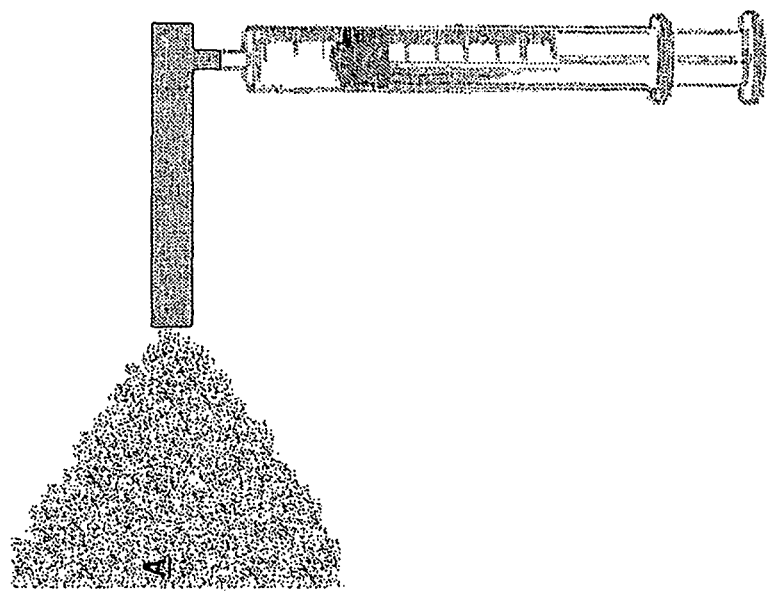
FIGS. 4A and 4B show each one a perspective view of the device of FIG. 1 during a respective use phase in combination with a syringe.

The sizes represented in the above-illustrated figures are to be meant by pure way of example and they are not necessarily shown in proportion.

DETAILED DESCRIPTION OF PREFERRED EMBODIMENTS

By firstly referring to FIGS. 1 to 3, a delivery device of a substance in the form of aerosol according to a preferred embodiment of the invention is designated as a whole with 1.

The device 1 comprises a main body constituted by an outer body 2 and an inner body 3 housed within the outer body. Both bodies 2 and 3 have a substantially oblong shape and they are arranged with their own prevailing development longitudinal axis substantially coincident with, or parallel to, a longitudinal axis L of the device 1.

Preferably, the bodies 2 and 3 have a substantially cylindrical overall geometry.

The outer body 2 is hollow and formed by a side skirt 20 and by a front face 21 bearing a dispensing nozzle 53, the latter with preferably rounded delivery section.

As better visible in FIG. 2D, the dispensing nozzle 53 is defined by walls 530 having substantially frustoconical geometry, the nozzle being obtained at a smaller base of the truncated cone.

The inner body 3 is defined by a side skirt 30 arranged within the skirt 20 of the outer body 2 in slightly eccentric position with respect thereto with respect to the longitudinal axis L. The inner body 3 has then a front face 31 arranged substantially parallel to the front face 21 of the outer body 2 and spaced apart therefrom by means of one or more spacing elements 6.

Preferably, the spacing element 6, or each spacing element, is manufactured in one piece or however made integral to the outer body 2.

The inner body 3 has then a rear face 32 closing the device 1 on the rear side.

In the herein considered preferred embodiment, the faces 21, 31 and 32 have substantially circular geometry.

The inner body 3, at its own side skirt 30, bears an annular recess 310, defined in particular by a substantially cylindrical bottom wall 311 and by two side walls resulting plain in the side or longitudinal view of FIGS. 1 and 3.

The device 1 comprises then connection means 4, which in the present example are obtained integrally to the side skirt 20 of the outer body 2. In particular, in the present example the connection means 4 comprises a coupling sleeve, designated too with 4, with substantially cylindrical geometry and arranged according to an axis T substantially orthogonal to the longitudinal axis L. The sleeve 4 bears an inner wall with section decreasing along the axis T, and in particular decreasing towards the side skirt 20 of the outer body 2. In the present example, such decreasing section is obtained by means of a stepped inner profile 40.

In the present preferred embodiment, the sleeve 4 is arranged at the recess 310 of the inner body 3.

Figure 4A:
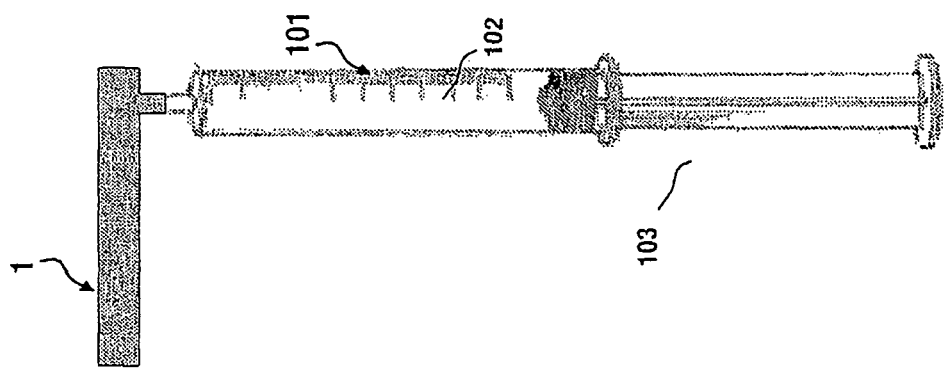
Figure 5:
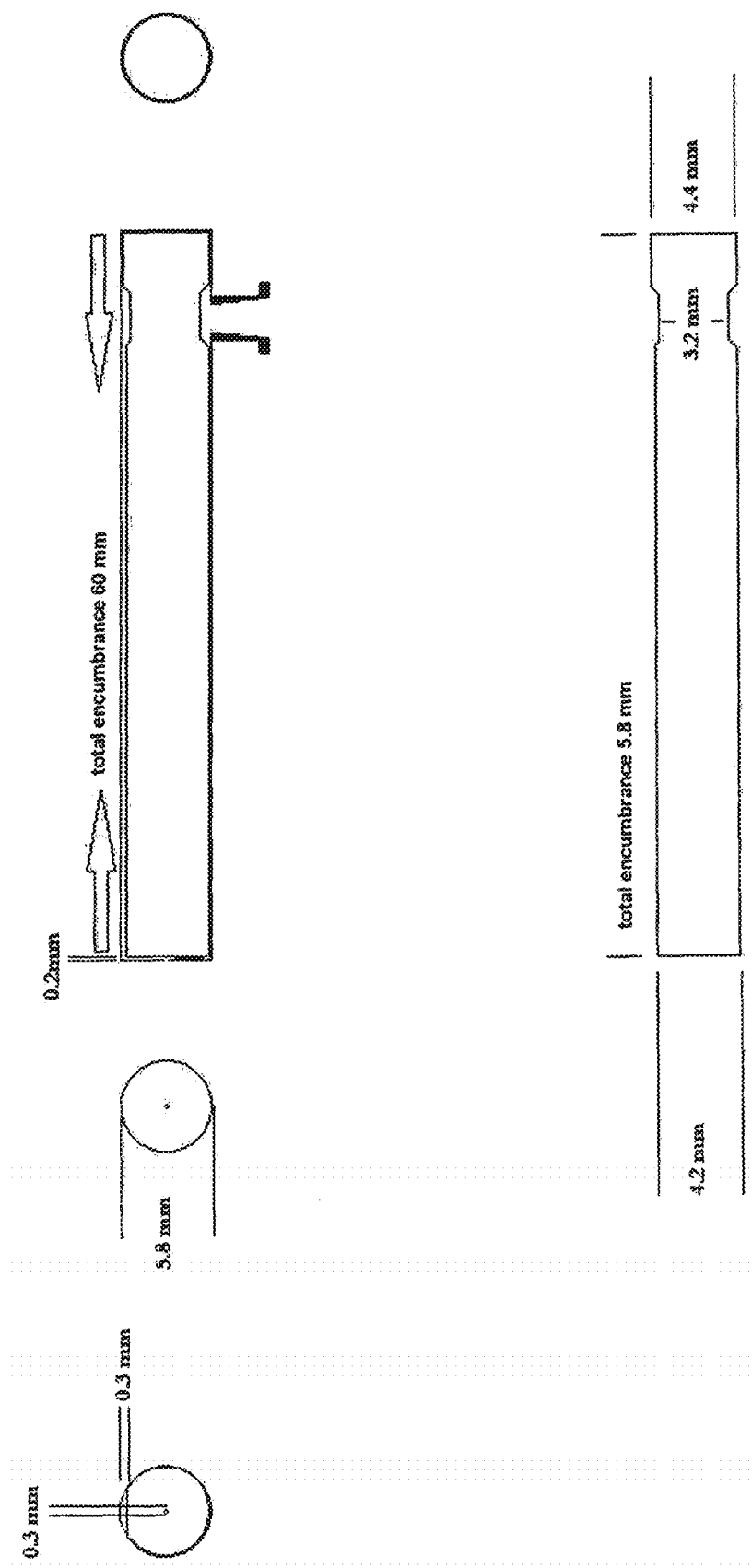
FIG. 5 shows the views of the preceding FIGS. 1 to 3 with indication of some preferred sizes.

As shown in FIGS. 4A and 4B, the sleeve 4 is used for connecting the device 1 to a syringe 101, the latter meant to contain a substance in liquid form. Preferably, such connection is of snap-in type, in particular a pressure snap-in, with the apex of the reservoir 102 of the syringe 101 received within the sleeve 4 itself.

The sleeve 4 can bear a peripheral flange, or ring, 41 suitable to establish the tight and/or connection with specific types of syringe.

The decentralized arrangement of the inner body 3 within the inner body 2 and the configuration of the device 1 described sofar makes that between outer body 2 and inner body 3 a fluidodynamic path 5 results to be defined, extending between the coupling sleeve 4 and the nozzle 53. Such path 5 is configured such that, in use, a manual actuation of the plunger 103 of the syringe 101 produces the input of the substance in liquid form from the reservoir 102 in the fluidodynamic path 5 through the coupling sleeve 4 and the outlet of the substance in the form of an aerosol (A) from the nozzle 53.

The fluid dynamic path comprises: first and second segments extending in a first direction perpendicular to the longitudinal direction, a third segment extending in a second direction parallel to the longitudinal direction, a fourth segment extending in a third direction perpendicular to the longitudinal direction and opposing the first direction, and a fifth segment extending in the second direction. The first segment includes the connection element with a flow therethrough in the first direction, the second segment includes the expansion chamber with a flow therethrough in the first direction, the third segment includes the acceleration chamber with a flow therethrough in the second direction, the fourth segment includes the passage with a flow therethrough in the third direction, and the fifth segment includes the dispensing nozzle with a flow therethrough in the second direction.

The path 5 is configured so as to produce globally, between the coupling sleeve 4 and the dispensing nozzle 53, an increase in the flow velocity of the substance and a reduction of its flow rate.

In the herein considered preferred embodiment, the fluidodynamic path 5 comprises a chamber 50 with substantially annular, preferably substantially toric, geometry defined between the recess 310 of the inner body 2 and the portion of the side skirt 20 of the outer body 2 facing on such recess 310.

The annular chamber 50, by intervening downstream of the inner adduction channel defined by the sleeve 4, represents an expansion chamber for the fluid.

Preferably, the path 5 comprises a tract or chamber 52 with development substantially rectilinear along the longitudinal axis L, preferably arranged immediately downstream of the chamber 50. In particular, such tract 52 is defined between the side skirts 20 and 30, substantially on the opposite side of the sleeve 4 and by virtue of the decentralized arrangement of the inner body 3 within the outer body 2. The longitudinal tract 52 defines a channel or chamber for accelerating the fluid, by virtue of the reduced cross section with respect to the chamber 50.

Downstream of such longitudinal tract 52, the fluidodynamic path provides then a cross portion 51, corresponding to the compartment defined between the two faces 21 and 31 and which ends in the nozzle 53.

The fluid path from the expansion chamber 50 and through the acceleration channel 52 and the outlet orifice 53 makes that the fluid itself reaches a speed sufficient to the nebulization in the form of an aerosol.

Based upon an embodiment variant, the syringe 101 can be replaced by any device bearing a container or reservoir of the substance in liquid form and manual actuation means apt to expel the substance from the container, the latter being constituted by a plunger or other.

Furthermore, between device 1 and syringe or other device, a permanent, instead of removable, connection can be provided.

Yet, the overall delivery system constituted by the device 1 and by reservoir, syringe, container or other can provide that the substance received in the latter is in form different from liquid, for example partially aeriform or nebulized.

Based upon an embodiment variant shown in FIGS. 8 and 8A, the device and the system described herein can be integrated with a sealing element 7, preferably shaped like a truncated cone and for example made of plastic, gummy or spongy material (FIG. 8A) with the function of "sealing" the device 1, in particular at the orifice 53, at the nostril and/or to avoid too deep insertions, and the outlet, by gravity and absorption, of the drug.

The described delivery system can be provided in form of kit, in case even with reservoir or container with different capacity and, based upon an embodiment variant, in conjunction with one or more substances to be administered. The latter can be provided already received in the container, for example in the body of syringe, which for example can be equipped with tight seals removable upon use.

FIGS. 6A and 6B show the results of preliminary delivery tests, wherein the better efficiency of the device 1 can be seen with respect to a known spray dispenser in terms of quantity and distribution of the substance.

Similarly, FIGS. 7A to 7D relate to preliminary delivery tests within the rhynosinusal cavities.

Figure 9D:
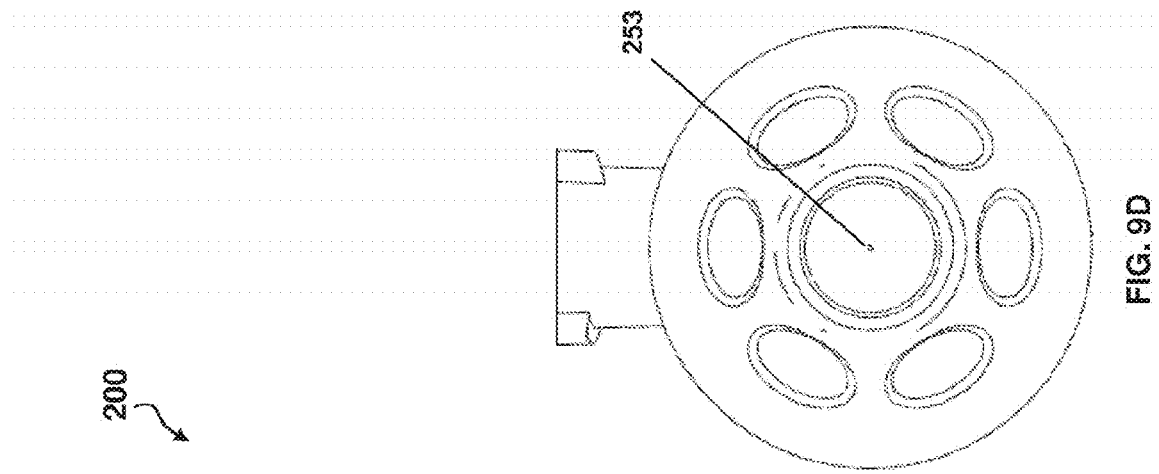
FIGS. 9A to 9D relate to another preferred embodiment of the device of the invention, showing a first and a second side view, a perspective view and a top plan view thereof, respectively.
Figure 9C:
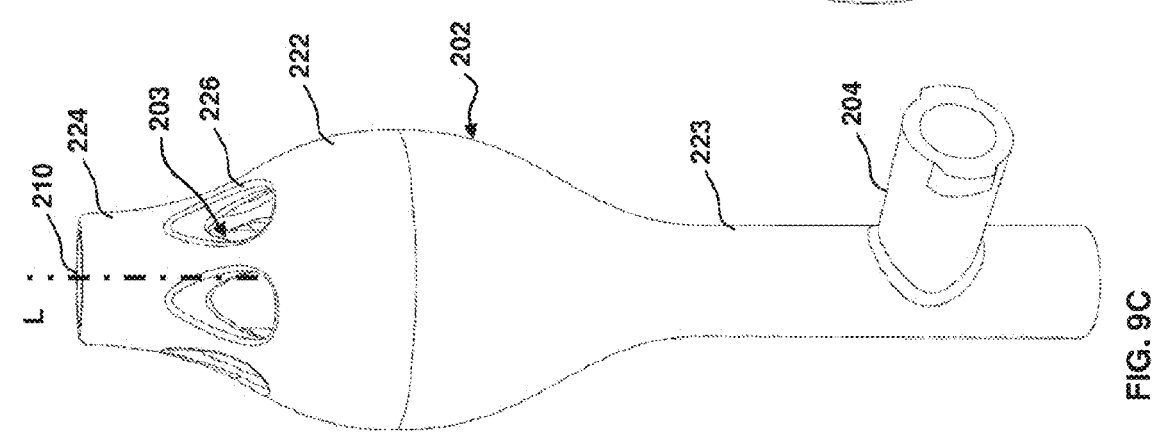
Figure 9B:
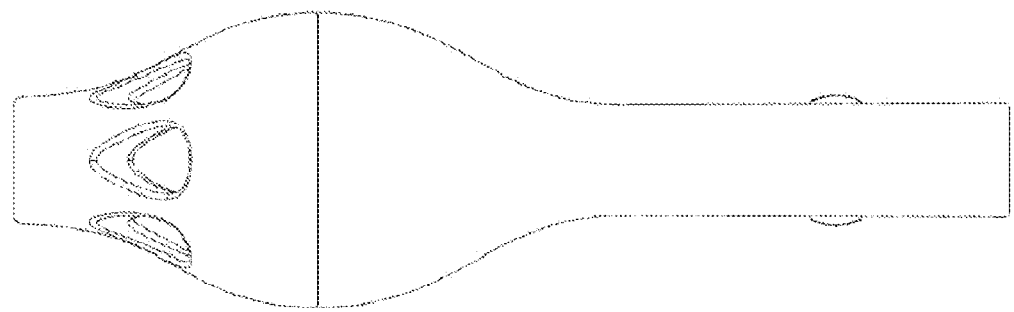
Figure 9A:
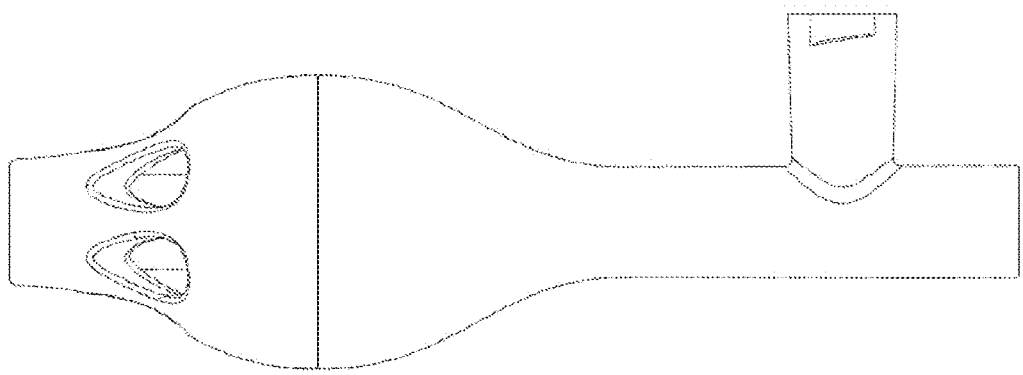
Figure 10:
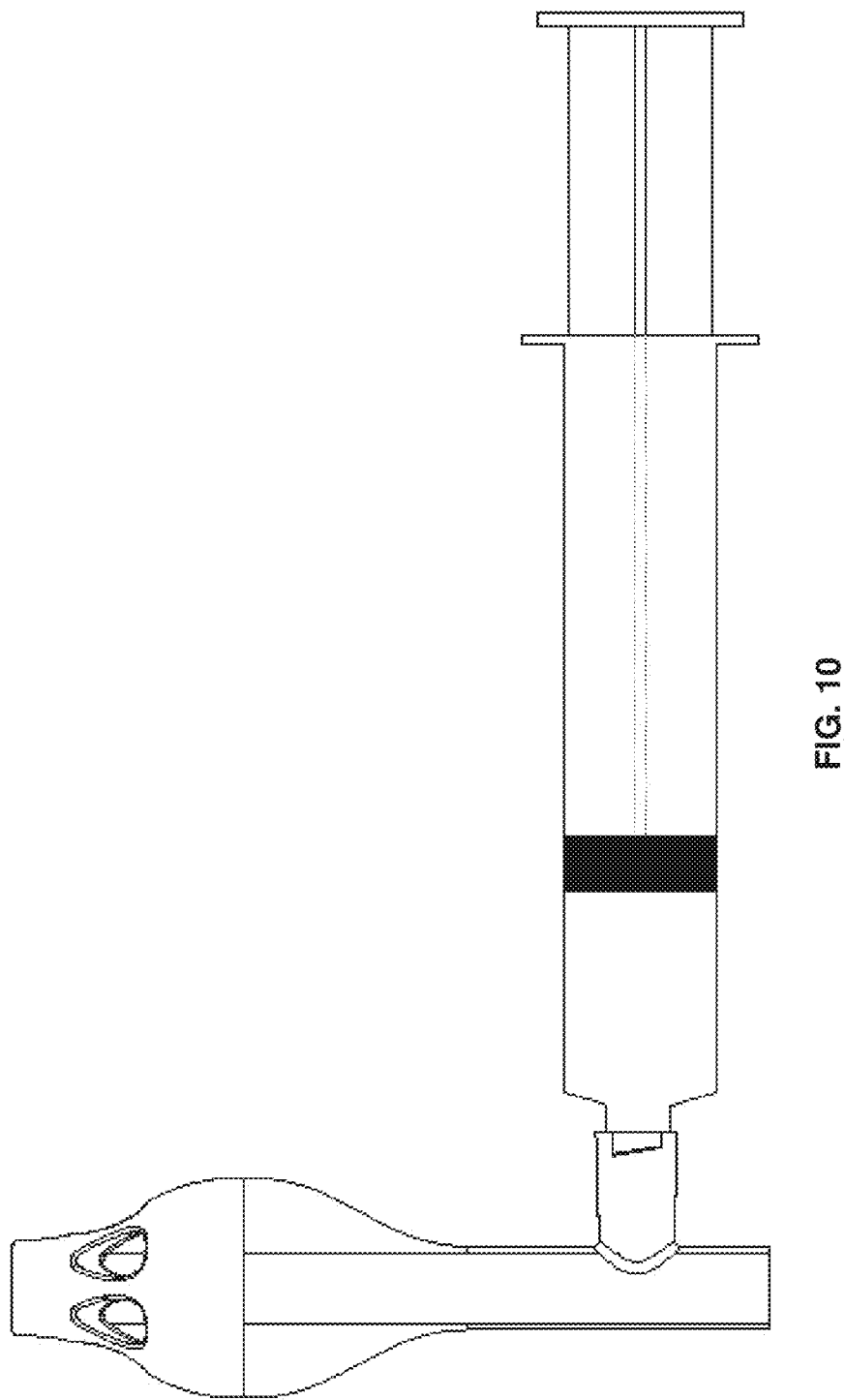
FIG. 10 shows a side view of the device of FIGS. 9A-9D, during a use in combination with a syringe.

With reference to FIGS. 9A to 10, an embodiment variant of the device of the invention will be now described. Such variant will be illustrated only in the differences with respect to what already described.

The device of the considered variant is designated as a whole with 200. The device 200 comprises a main body constituted by an outer body 202 and by an inner body 203 housed within the outer body. Both bodies 202 and 203 have a substantially oblong shape and they are arranged with their own prevailing development longitudinal axis coincident with, or parallel to, a longitudinal axis L of the device 200.

Preferably, the inner body 203 has substantially cylindrical overall geometry.

On the contrary, the outer body 202 bears a portion 222 with rounded profile. In the present example, such portion 222 implements as a whole an ampulla-like shape. The portion 222 is interposed between two end portions of the outer body 202, respectively a distal portion 223 and a proximal portion 224 with respect to the user receiving the treatment. Such two distal 223 and proximal 224 portions have a restricted cross-section with respect to the rounded portion 222 and in particular a substantially cylindrical geometry.

The outer body 202 is hollow and bears a front face 210, arranged at the proximal portion 224, having a dispensing nozzle 253 analogous to the one already described for the first embodiment.

At the rounded portion 222 the outer body 202 bears a plurality of openings 226 to receive possible refluent fluid outgoing from the nostril. Through such openings 226, the refluent fluid is received in an inner container of the device 200. The container then can be emptied selectively by turning around the device, and then through the openings 226, or by allowing a removable connection of the portions 224 and 222 to the portion 223 of the outer body 202. The container can have a rounded and/or (almost) spherical shape, by following the profile of the portion 222, or oblong shape or with any other geometry. Furthermore, the container can be made at least partially by means of the walls of the portion 222 or be provided as a distinct component.

The rounded portion 222 implements even a kind of "stop" which does not allow pushing the device 200, and in particular the portion 224, too much inside the nostril.

The device 200 comprises then connection means 204, substantially analogous to the already described ones.

The ergonomics of the device will be appreciated, also due to the coupling simplicity between device itself and container of the substance.

It will be further appreciated that the person skilled in the art can modulate the properties of the fluidodynamic path according to the specific nebulization needs, and in particular to the wished sizes for the particles and the specific viscosity features of the substance to be nebulized.

The device of the invention, given the speed imparted to the fluid thanks to the toroidal expansion chamber ending in a path with very small diameter, can nebulize even viscous solutions constituted by macromolecules with sizes larger than 1000 kDa. The nebulization results to be constituted by particles which by more than 95% exceed 10 micron of diameter.

The present invention has been sofar described by referring to preferred embodiments. It is to be meant the other embodiments belonging to the same inventive core may exist, as defined by the protection scope of the here-below reported claims.

The invention claimed is:

1. A delivery device, of a substance in the form of aerosol, configured to be used in combination with a container of the substance in liquid form and with a manual actuation system configured to expel the substance from the container in combination with a syringe, said delivery device comprising:
   a connection element configured to connect the device with the container;
   an elongated outer body bearing a dispensing nozzle for dispensing the substance in the form of an aerosol, the elongated outer body extending in a longitudinal direction and having a centrally extending longitudinal axis;
   an inner body, received within said elongated outer body, said inner body including a first face at a distal end of said inner body, said elongated outer body including a second face at a distal end of said elongated outer body, said first face being spaced apart from said second face to define a passage therebetween; and
   a fluid-dynamic path comprised between said connection element and said dispensing nozzle and defined between said elongated outer body and said inner body, which fluid-dynamic path is configured such that, in use, a manual actuation of a manual actuator produces an input of the substance in liquid form in said fluid-dynamic path through said connection element and an output of the substance in the form of an aerosol through said dispensing nozzle, said fluid-dynamic path comprising;
   first and second segments extending in a first direction perpendicular to the longitudinal direction;
   a third segment extending in a second direction parallel to the longitudinal direction;
   a fourth segment extending in a third direction perpendicular to the longitudinal direction and opposing the first direction;
   a fifth segment extending in the second direction;
   wherein the first segment includes the connection element, with a flow therethrough in the first direction;
   wherein the second segment includes an expansion chamber, with a flow therethrough in the first direction, the expansion chamber arranged immediately downstream relative to said connection element with respect to the flow of the substance within the delivery device and having a toroidal shape between the elongated outer body and the inner body, the connection element having a decreasing cross-section in the first direction; and
   wherein the third segment includes an acceleration chamber, with a flow therethrough in the second direction, the acceleration chamber arranged immediately downstream relative to said expansion chamber with respect to the flow of the substance within the delivery device and having an elongated geometry, said acceleration chamber extending in the second direction and having an eccentric position relative to the centrally extending longitudinal axis;
   wherein the fourth segment includes the passage, with a flow therethrough in the third direction;
   wherein the fifth segment includes the dispensing nozzle, with a flow therethrough in the second direction.

2. The delivery device according to claim 1, wherein said fluid dynamic path is configured to produce, between said connection element and said dispensing nozzle, an increase in the flow velocity of the substance and a reduction of a flow rate.

3. The delivery device according to claim 1, wherein said dispensing nozzle is defined by walls presenting a frusto-conical geometry reproducing a truncated cone, said dispensing nozzle being obtained at a smaller base of the truncated cone.

4. The delivery device according to claim 1, wherein said connection element comprises a coupling element, in the form of a sleeve, adapted to receive a snap-in end of the container of the substance in liquid form.

5. The delivery device according to claim 1, wherein at least one chosen from said elongated outer body and said inner body have an oblong shape, presenting a cylindrical geometry.

6. The delivery device according to claim 1, wherein said inner body is arranged off-center with respect to said elongated outer body in such a way that between them an acceleration chamber remains defined.

7. The delivery device according to claim 1, which is of a disposable type.

8. The delivery device according to claim 1, wherein said elongated outer body comprises a rounded portion suitable to act as a stop to limit a penetration of the delivery device within a nostril.

9. The delivery device according to claim 1, comprising a container arranged so as to gather refluent fluid outgoing from a nostril.

10. The delivery device according to claim 1, wherein said elongated outer body includes one or more openings for gathering refluent fluid outgoing from a nostril.

11. The delivery device according to claim 1, and further comprising a container of the substance in liquid form and a manual actuation system configured to expel the substance from the container, wherein said container is a body of a syringe having a plunger.

* * * * *